United States Patent
Walia

[19]

[11] Patent Number: 5,915,964
[45] Date of Patent: Jun. 29, 1999

[54] FLEXIBLE GUIDED FILE FOR ROOT CANAL PROCEDURES

[76] Inventor: Harmeet Walia, 611 Bridlewood La., Oak Creek, Wis. 53154

[21] Appl. No.: 09/021,336

[22] Filed: Feb. 10, 1998

Related U.S. Application Data

[63] Continuation-in-part of application No. 08/729,123, Oct. 11, 1996, abandoned.

[51] Int. Cl.$^6$ ........................................... A61C 5/02
[52] U.S. Cl. ........................................... 433/102; 433/224
[58] Field of Search ................... 433/102, 165, 433/166, 224; 606/83

[56] References Cited

U.S. PATENT DOCUMENTS

| | | | |
|---|---|---|---|
| 3,318,000 | 5/1967 | Paris | 433/224 |
| 3,330,040 | 7/1967 | Kahn | 433/224 |
| 3,534,476 | 10/1970 | Winters | 433/224 |
| 4,299,571 | 11/1981 | McSpadden | 433/102 |
| 4,337,038 | 6/1982 | Saito et al. | 433/102 |
| 5,273,519 | 12/1993 | Koros et al. | 606/83 |
| 5,540,587 | 7/1996 | Malmin | 433/224 |

FOREIGN PATENT DOCUMENTS

| | | | |
|---|---|---|---|
| 2616652 | 12/1988 | France | 433/224 |
| 672313 | 2/1939 | Germany . | |
| 3618879 | 9/1987 | Germany | 433/102 |
| 4003748 | 8/1991 | Germany | 433/102 |

OTHER PUBLICATIONS

H. Walia, et al., "An Initial Investigation of the Bending and Torsional Properties of Nitonol Root Canal Files," *J. Endodontics* 14(7):346–351, 1988.

*Primary Examiner*—Ralph A. Lewis
*Attorney, Agent, or Firm*—Quarles & Brady

[57] ABSTRACT

An endodontic file assembly includes a noncutting file guide along which a flexible file may run. The guide is first inserted into the root canal anchored at its tip and the file subsequently moved along the guide. Disproportionate forces between the file and inner and outer curvatures of the root canal caused by the natural resilience of the file are thereby reduced to provide for more uniform debridement of the inner walls of the root canal.

12 Claims, 4 Drawing Sheets

FLEXIBLE GUIDED FILE FOR ROOT CANAL PROCEDURES

CROSS REFERENCED TO RELATED APPLICATIONS

This application is a continuation-in-part of U.S. application Ser. No. 08/729,123 filed Oct. 11, 1996, now abandoned.

FIELD OF THE INVENTION

The present invention relates to tools used in the field of dentistry and endodontics and, in particular, to a file for enlarging root canals in preparation for root canal therapy.

BACKGROUND OF THE INVENTION

When a tooth experiences trauma such as having become infected or having a nerve in the root adversely affected by proximity to a deeply set filling, the body (dental pulp) takes defensive measures to constrict the root canal to isolate it or its defenses may be overcome by the irritant. If the diagnostic tests of the tooth reveal irreversible damage, a root canal or endodontic procedure is indicated.

The well known root canal procedure is initiated by drilling a hole inwardly from the crown of the tooth in line with the canal of interest. Then files and reamers of increasing larger diameters are used to clean out the canal until it presents a wall of clean dentine and is enlarged sufficiently to be filled with an inert material and then sealed. In cleaning out the canal, it is important that the clinician not change the general shape of the canal such as by creating a ledge in it or by changing its curvature since if either of these events occur, there is an increased probability that one of the successively larger and stiffer files used to clean the canal will perforate the root wall. This in most cases requires surgical correction or extraction of the tooth.

The risk of the tooth canal becoming improperly contoured or perforated is reduced somewhat by the use of files constructed of nickel titanium which are more flexible than previous stainless steel files. Even so, with either type of file, there is a tendency for the file to remove more material from the outer curvature of the root wall than the inner curvature of the root wall as a result of the stiffness of the file. This problem is more likely to occur with larger files.

Some clinicians try to overcome this problem of the file not following the root curve by pre-curving 2–4 mm of the tip of the larger and stiffer files. Some clinicians also file away at the cutting flutes along one side of the file. This way they hope to avoid excessive cutting on the concave or outside curve of the canal.

SUMMARY OF THE INVENTION

The present invention reduces the tendency of flexible files to preferentially cut the outer curvature of a root canal by providing a guide that may be inserted into the root canal to extend between the root tip and the crown of the tooth and to provide a surface other than the wall of the root canal that guides the file along the curved trajectory of the root canal. The guide may include an anchor at its tip to resist displacement with respect to the tooth when the file is moved along the guide.

Specifically, the present invention provides endodontic file assembly having an elongate guide sized to fit within a root canal of a tooth as inserted through the tooth's crown along a root canal toward a root tip of the tooth. The guide includes an anchor engaging the tooth at the root tip to resist withdrawal of the guide with respect to the tooth. A flexible cutter or file, having an outwardly extending cutting surface positioned to contact a wall of the root canal when the file is in position within the root canal, includes a guide engaging surface which slidably holds the file to move along the elongate guide when the elongate guide is positioned within the root canal.

Thus it is one object of the invention to substitute a separate guide, following the curvature of the root canal, for the root canal walls as a means for causing the file to curve along the root canal. Because the file is curved by the action of the guide, the force between the walls of the root canal and the file is equalized promoting more even cutting of the inner and outer curvatures of the root canal.

In one embodiment, the guide engaging surface is a bore through the file through which the elongate guide may pass.

Thus it is another object of the invention to provide a simple guiding mechanism suitable for many sizes of endodontic files.

The elongate guide may include a stop limiting sliding motion of the file along the elongate guide past the root tip when the elongate guide is inserted in the root canal. The elongate guide may also include a stop limiting insertion of the elongate guide pass the root tip.

Thus it is another object of the invention to limit possible filing incursions into the supporting tissue of the tooth or a jamming of the file in the root tip.

The foregoing and other objects and advantages of the invention will appear from the following description. In this description, reference is made to the accompanying drawings which form a part hereof and in which there is shown by way of illustration, a preferred embodiment of the invention. Such embodiment does not necessarily represent the full scope of the invention, however, and reference must be made therefore to the claims for interpreting the scope of the invention.

DETAILED DESCRIPTION OF THE PREFERRED EMBODIMENT

Figure 1:
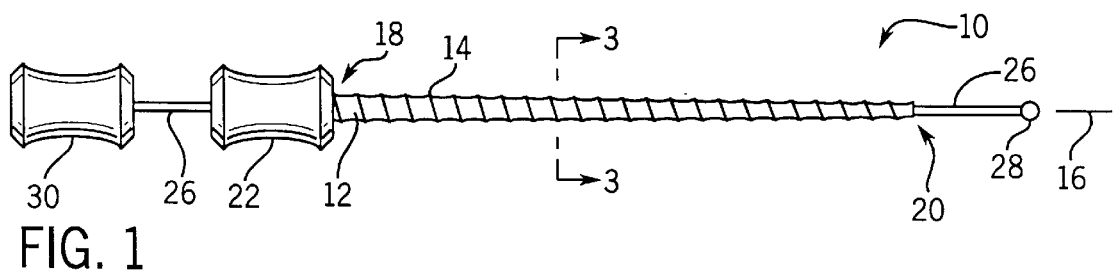
FIG. 1 is a view of a first embodiment of the invention where an elongate guide fits within a hollow core of an endodontic file.

Referring to FIG. 1, a file assembly 10 includes a file body 12 having radially extending flutes 14 disposed along an axis 16 of the file body to provide an outer cutting surface. The file body 12 may be constructed of a nickel titanium alloy known by the tradename of Nitinol or of stainless steel, both of which are now well known in the art for endodontic files.

File body 12 tapers generally to a narrower diameter from its shank end 18 to its point end 20. The taper is normally 0.02 mm of taper per millimeter of working length and the tip diameter of the file may range from 0.01 mm to 1.2 mm. At the shank end 18, the file body 12 is received by a molded plastic grip 22 sized to be received between thumb and forefinger of a clinician. The length of the file body 12 along the axis 16 is comparable to standard endodontic files and is sufficient to extend the full length of the root canal of a typical tooth.

Figure 3:
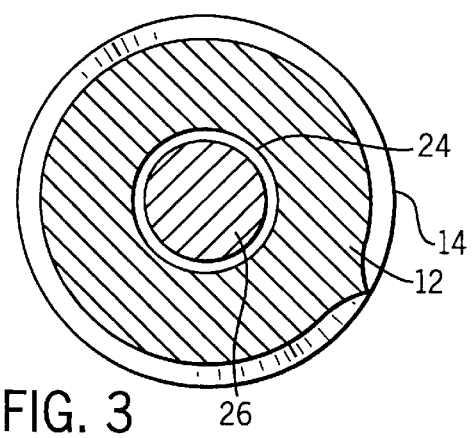
FIG. 3 is a cross-sectional view along line 3—3 of FIG. 1 showing the guide fitting within the hollow bore of the file.
Figure 4:
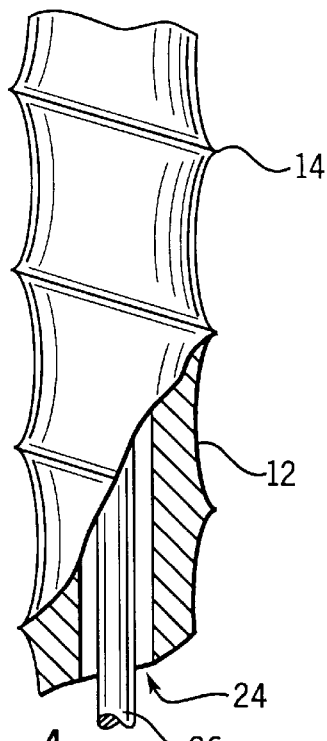
FIG. 4 is a fragmentary view of the body of the file of FIG. 1 in partial cross-section.

Referring also to FIG. 3, the file body 12 includes a central bore 24 extending along its entire length along axis 16 and continued through grip 22. The bore 24 is sized to receive a stainless steel guide wire 26 of sufficient length to extend out of grip 22 at the shank end of the file body 12 and at the same time beyond the point end 20 of the file body 12. The portion of the guide wire extending outward from the point end 20 includes a root tip stop 28 as will be described further below. The end of the guide wire 26 extending from the grip 22 is attached to its own grip 30 substantially identical to the grip 22 in outer dimensions.

Figure 5:
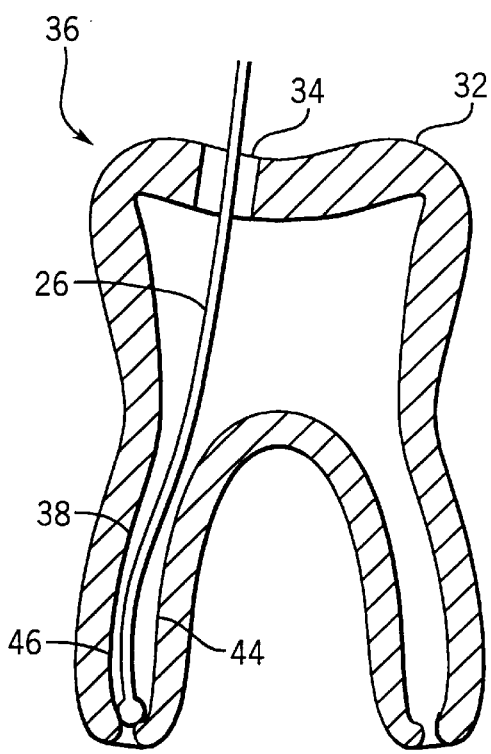
FIG. 5 is a cross-section of a tooth showing placement of the guide in the root canal prior to insertion of the file.

Referring now to FIG. 5, a tooth 32 may be prepared for the root canal procedure by the introduction of a bore 34 through the crown 36 of the tooth and the removal of material within the crown by a rotating burr or the like. The root canal 38 is then enlarged to an initial diameter suitable for receiving the guide wire 26 by a conventional small diameter nickel titanium file or the like.

Figure 6:
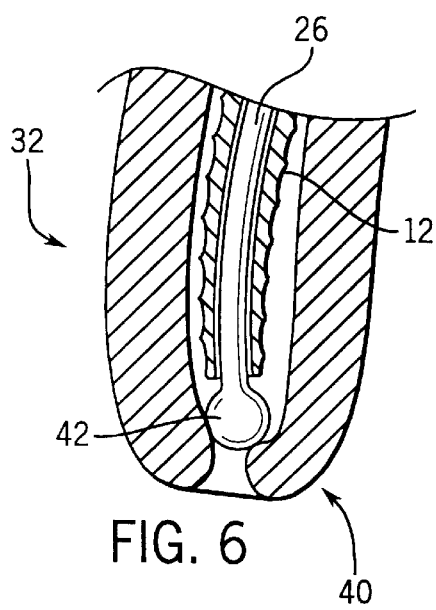
FIG. 6 is a detailed view of the root tip of the tooth of FIG. 5 showing a stop on the guide limiting the insertion depth of the guide and the furthest excursion of the file as guided by the guide.
Figure 7:
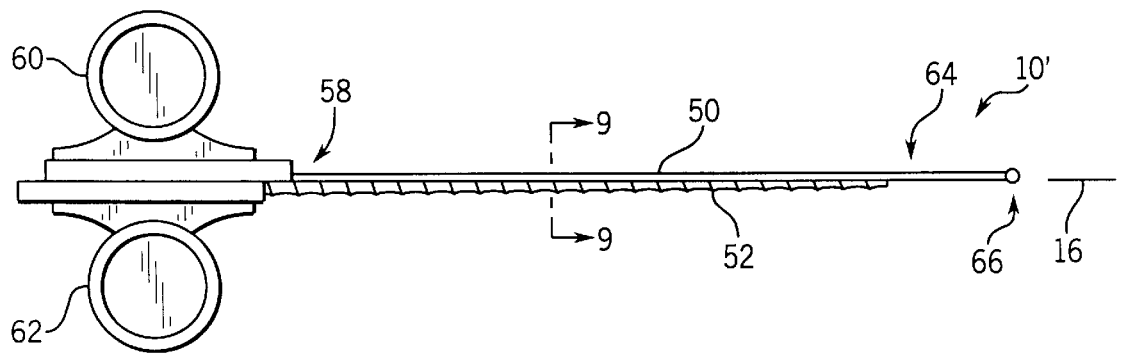
FIG. 7 is a view similar to FIG. 1 of an alternative embodiment of the invention in which the guide is positioned to one side of the file.
Figure 8:
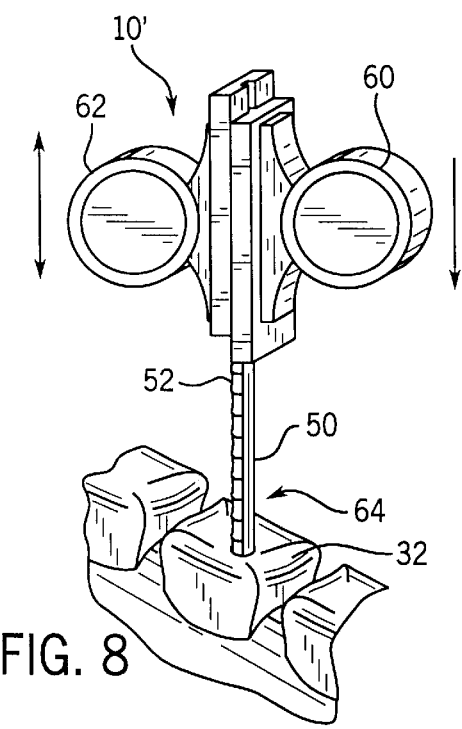
FIG. 8 is a figure similar to that of FIG. 2 for the alternative embodiment.
Figure 9:
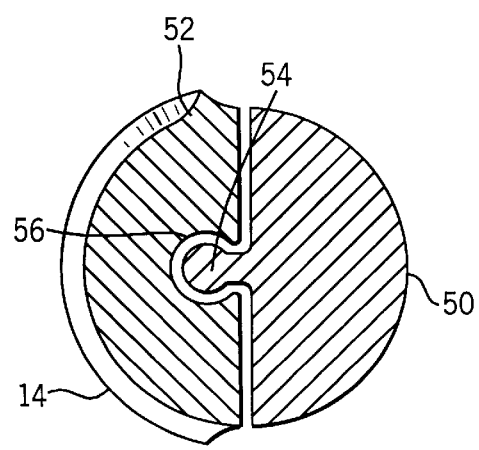
FIG. 9 is a cross-sectional view along lines 9—9 of FIG. 7.
Figure 10:
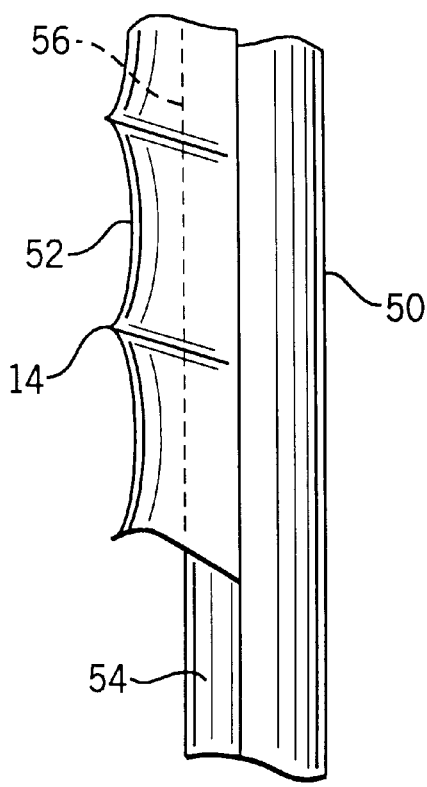
FIG. 10 is a figure similar to that of FIG. 4 but showing the alternative embodiment.

Referring also to FIG. 6, the guide wire 26 is then inserted down through the bore 34 in the crown 36 and into the root canal 38 and a working length established by radiograph so that the guide wire stops at the root tip 40.

Figure 2:
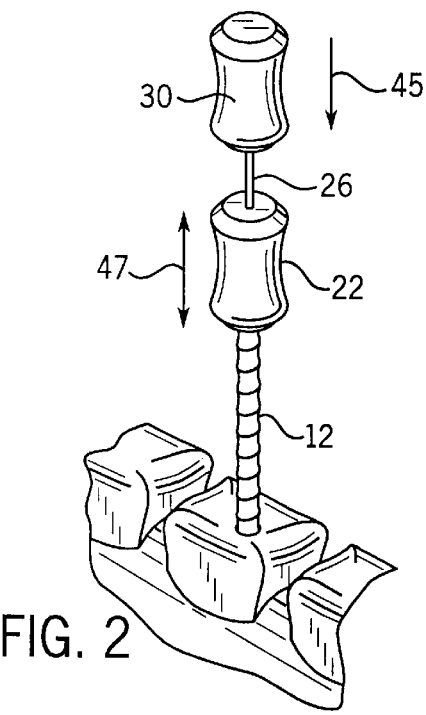
FIG. 2 is perspective view of the file assembly of FIG. 1 in place within a tooth.

As shown in FIG. 2, a slight downward pressure 45 is then exerted on the guide wire 26 by means of grip 30 to hold the stop 42 into abutment with the root tip 40. Axially reciprocating motion 47 may be imparted to the file body 12 by means of grip 22 causing the file body 12 to pass upward and downward along the guide wire 26 through the root canal 38. Curvature of the file body 12 is enforced by the guide wire 26 thus promoting more even cutting of the inner curvature 44 and the outer curvature 46 of the root canal. Further, the stop 42 limits downward motion of the file body 12 and, in so far as stop 42 may not proceed out of the root tip 40, limits excursions of the file body 12 into the supporting tissue of the tooth. The grip 22 is sized so that it may be gripped by a chuck of a standard rotary handpiece so as to be given a rotary motion about the guide wire 26.

Referring now to FIGS. 7, 8, 9 and 10 in an alternative embodiment of the invention, a guide 50 lies along side a file body 52, the latter file body 52 being held against the guide 50 by means of a dovetail joint formed of a bulbous rail 54 extending along the axis 16 of the file body and received in a corresponding slot 56 cut into the file body 52. The bulb portion of the rail 54 prevents disengagement of the guide 50 from the file body 52 in a direction perpendicular to axis 16.

Flutes 14 of the file body 52 thus cover approximately half the outer circumference of the combined file body 52 and guide 50 but are not present on the outer surface of the guide 50. The direction of cutting of the file assembly 10' thus may be accurately controlled by controlling the rotational orientation of the file body 52 about the axis 16. Tang ends 58 of the file body 12 and guide 50 are received by corresponding grips 60 and 62 continuing an interlocking dovetail of the file body 52 and the guide 50 so as to prevent unintentional separation of the two. The grips 60 and 62 are tactilely asymmetric so as to permit a ready adjustment of the angular orientation of the file assembly 10' about axis 16 depending on the direction cutting is required. A point end 64 of the guide 50 includes a stop 66 operating analogously to the stop 42 described with respect to FIG. 6.

Figure 11:
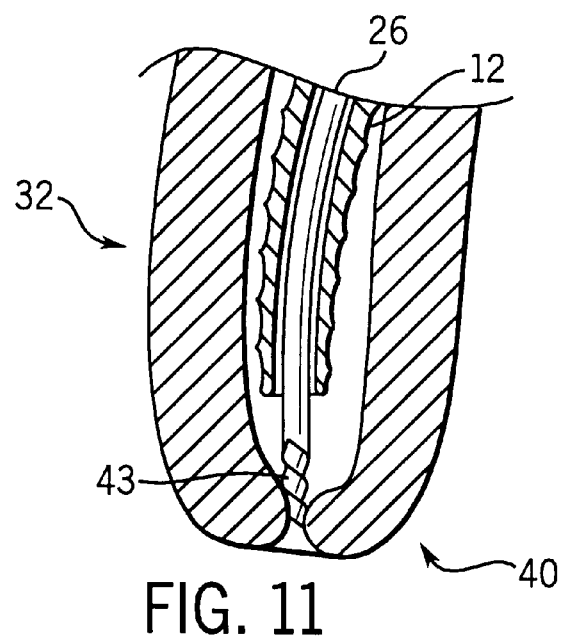
FIG. 11 is a figure similar to that of FIG. 6 showing anchoring teeth positioned at the tip of the wire guide to resist a pulling out of the wire guide caused by forces from the file.

Referring now to FIG. 11, the guide wire 26 may include anchoring teeth 43 formed in its tip using the same forming methods used to construct file teeth on the file body 12. The anchoring teeth 43 may be locked to the root tip 40 to resist a pulling out of the guide wire 26 as the file body 12 passes upward and downward along the guide wire 26 through the root canal 38. Without anchoring, the guide wire 26 may pull up or kink at the advancing tip of the file body 12 or by flexing and pulling away, fail to provide sufficient guidance for the file body 12 as is necessary to have the file body curve properly along the root canal 38. At the conclusion of the procedure, the guide wire 26 may be released from the root tip 40 by additional tension placed on the wire guide 26 from its exposed end.

The above description has been that of a preferred embodiment of the present invention. It will occur to those that practice the art that many modifications may be made without departing from the spirit and scope of the invention. As used herein, files should refer generally to instruments used for enlarging root canals including reamers, burrs and the like. It will be understood that the guide wire may be suitable not only for reciprocating instruments but also employing a rotary motion as they progress down the root canal. In order to apprise the public of the various embodiments that may fall within the scope of the invention, the following claims are made.

I claim:

1. An endodontic cutter assembly comprising:
   an elongate guide sized to fit within a root canal of a tooth as inserted through the tooth's crown along a root canal toward a root tip of the tooth, the guide including an anchor portion having teeth adapted to anchor to the tooth at the root tip to resist withdrawal of the guide with respect to the tooth; and
   a flexible file extending from a shank end to a point end and having outwardly extending cutting flutes over the length of the file between shank end and point end, the flutes positioned to contact a wall of the root canal when the cutter is positioned within the root canal, the cutter further having an inwardly facing guide engaging surface slidably holding the cutter to move along the elongate guide when the elongate guide is positioned within the root canal.

2. The endodontic cutter assembly of claim 1 wherein the guide engaging surface is a bore through the cutter through which the elongate guide may pass.

3. The endodontic cutter assembly of claim 2 wherein the cutter includes a shank portion adapted to be received by a rotary handpiece.

4. The endodontic cutter assembly of claim 1 wherein anchor is a set of teeth formed in an end of the guide.

5. The endodontic cutter assembly of claim 4 wherein the elongate guide includes a tactilely marked handle identifying rotational orientation of the elongate guide within the root canal.

6. The endodontic cutter assembly of claim 1 wherein the elongate guide includes a stop limiting sliding motion of the cutter along the elongate guide past the root tip when the elongate guide is inserted in the root canal.

7. The endodontic cutter assembly of claim 1 wherein the elongate guide includes a stop limiting insertion of the elongate guide past the root tip.

8. The endodontic cutter assembly of claim 1 wherein the cutter is composed of nickel titanium alloy.

9. The endodontic cutter assembly of claim 1 wherein the flexible cutter is a tubular file having a central lumen forming the inwardly facing guide engaging surface.

10. The endodontic cutter assembly of claim 1 wherein the flexible cutter is a file 56 having a slot engaging and partially surrounding the elongate guide.

11. A method of performing a root canal procedure on a tooth having a root canal terminating in a root tip and employing an endodontic cutter assembly having:

an elongate guide sized to fit within a root canal of a tooth as inserted through the tooth's crown along a root canal toward a root tip of the tooth, the guide including an anchor having teeth adapted to anchor the tooth at the root tip to resist withdrawal of the guide with respect to the tooth; and a flexible file having an outwardly extending cutting surface extending over its length and positioned to contact a wall of the root canal when the cutter is positioned within the root canal, the cutter further having an inwardly facing guide engaging surface slidably holding the cutter to move along the elongate guide when the elongate guide is positioned within the root canal, the method comprising the steps of:
   (a) enlarging the root canal to a first dimension to receive the elongate guide;
   (b) inserting the elongate guide into the root canal to substantially the root tip;
   (c) anchoring a first end of the elongate guide to the root tip;
   (d) engaging the cutter with the elongate guide; and
   (e) reciprocating the cutter along the root canal as guided by the elongate guide.

12. The method of claim 11 wherein the cutter includes a shank portion adapted to be received by a rotary handpiece and wherein step (a) involves manipulating the cutter with a rotary handpiece.

* * * * *